United States Patent
Ogino et al.

(10) Patent No.: US 10,492,678 B2
(45) Date of Patent: Dec. 3, 2019

(54) IMAGE CAPTURING APPARATUS, IMAGE PROCESSING APPARATUS AND IMAGE PROCESSING METHOD FOR SECURE PROCESSING OF BIOLOGICAL INFORMATION

(71) Applicant: PANASONIC INTELLECTUAL PROPERTY MANAGEMENT CO., LTD., Osaka (JP)

(72) Inventors: Ryoji Ogino, Kanagawa (JP); Tsuyoshi Nakamura, Fukuoka (JP); Junya Kuwada, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 215 days.

(21) Appl. No.: 15/529,672

(22) PCT Filed: Dec. 7, 2015

(86) PCT No.: PCT/JP2015/006062
§ 371 (c)(1),
(2) Date: May 25, 2017

(87) PCT Pub. No.: WO2016/098308
PCT Pub. Date: Jun. 23, 2016

(65) Prior Publication Data
US 2017/0325680 A1 Nov. 16, 2017

(30) Foreign Application Priority Data
Dec. 17, 2014 (JP) ................. 2014-255461

(51) Int. Cl.
*G06K 9/00* (2006.01)
*G06K 9/46* (2006.01)
(Continued)

(52) U.S. Cl.
CPC ............. *A61B 3/102* (2013.01); *A61B 1/041* (2013.01); *A61B 1/3137* (2013.01); *A61B 5/00* (2013.01);
(Continued)

(58) Field of Classification Search
CPC ................. G06K 2009/00939; G06K 9/4652
See application file for complete search history.

(56) References Cited

U.S. PATENT DOCUMENTS

| 2005/0054935 A1* | 3/2005 | Rice ..................... A61B 5/0059 600/473 |
| 2009/0087028 A1* | 4/2009 | Lacey ................ G06K 9/00355 382/103 |

(Continued)

FOREIGN PATENT DOCUMENTS

| JP | 02-155381 | 6/1990 |
| JP | 2000-197011 | 7/2000 |

(Continued)

OTHER PUBLICATIONS

International Search Report (ISR) in International Pat. Appl. No. PCT/JP2015/006062, dated Feb. 23, 2016.

*Primary Examiner* — Gandhi Thirugnanam
(74) *Attorney, Agent, or Firm* — Greenblum & Bernstein, P.L.C.

(57) ABSTRACT

An image processing apparatus includes an image input that receives input of image data of a captured human being, a region detector that detects a specific color region of the image data, a filter that smooths a pixel value in the specific color region detected by the region detector by using a frame of the image data input into the image input and each of previous and subsequent frames of the image data of the inputting into the image input, a coder that codes an output image of the filter, and an output that outputs the output image of the filter coded by the coder.

4 Claims, 10 Drawing Sheets

(51) Int. Cl.
- *A61B 3/10* (2006.01)
- *A61B 5/00* (2006.01)
- *A61B 5/02* (2006.01)
- *A61B 1/04* (2006.01)
- *A61B 1/313* (2006.01)

(52) U.S. Cl.
CPC ............ *A61B 5/02* (2013.01); *G06K 9/00234* (2013.01); *G06K 9/00885* (2013.01); *G06K 9/00906* (2013.01); *G06K 9/4652* (2013.01); *G06K 2009/00939* (2013.01)

(56) References Cited

U.S. PATENT DOCUMENTS

| | | | | |
|---|---|---|---|---|
| 2012/0195469 | A1* | 8/2012 | Kirenko | G06T 7/20 382/103 |
| 2013/0083155 | A1* | 4/2013 | Andresen | H04L 12/1818 348/14.08 |
| 2013/0226007 | A1* | 8/2013 | Jeanne | A61B 6/5288 600/473 |
| 2013/0322729 | A1* | 12/2013 | Mestha | A61B 5/02 382/134 |
| 2015/0016746 | A1* | 1/2015 | Tsubota | G06T 3/00 382/275 |
| 2015/0085943 | A1* | 3/2015 | Taniguchi | H04N 5/21 375/240.29 |
| 2015/0287187 | A1* | 10/2015 | Redtel | G16H 40/67 382/128 |
| 2016/0048944 | A1* | 2/2016 | Ashmole | A61B 6/032 382/131 |
| 2017/0325680 | A1* | 11/2017 | Ogino | A61B 5/00 |

FOREIGN PATENT DOCUMENTS

| | | |
|---|---|---|
| JP | 2010-051592 | 3/2010 |
| JP | 2013-240039 | 11/2013 |
| JP | 2014-502187 | 1/2014 |

* cited by examiner

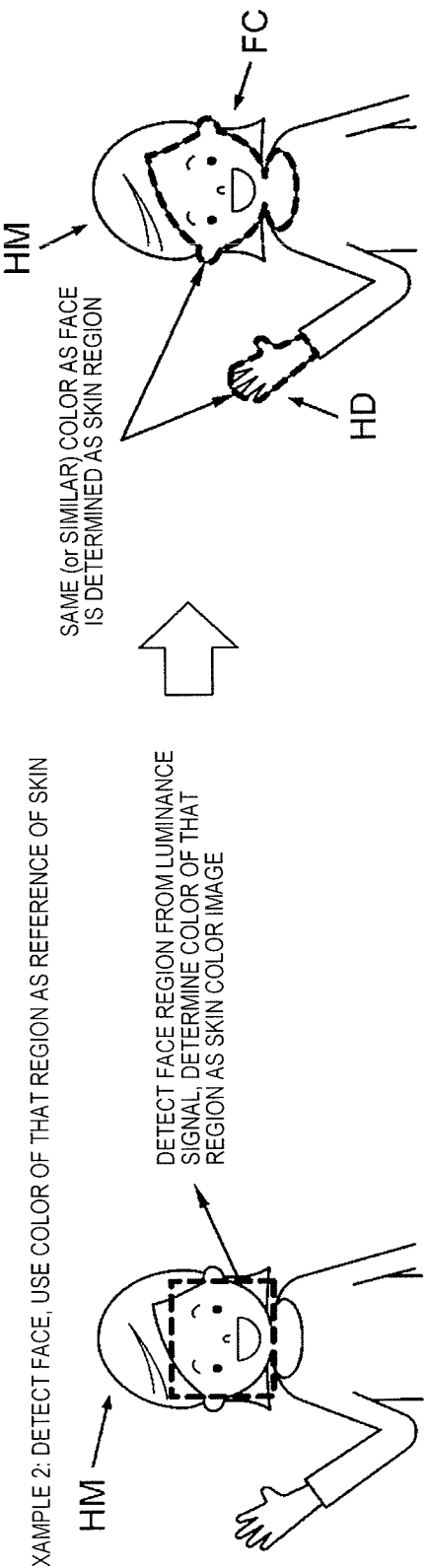

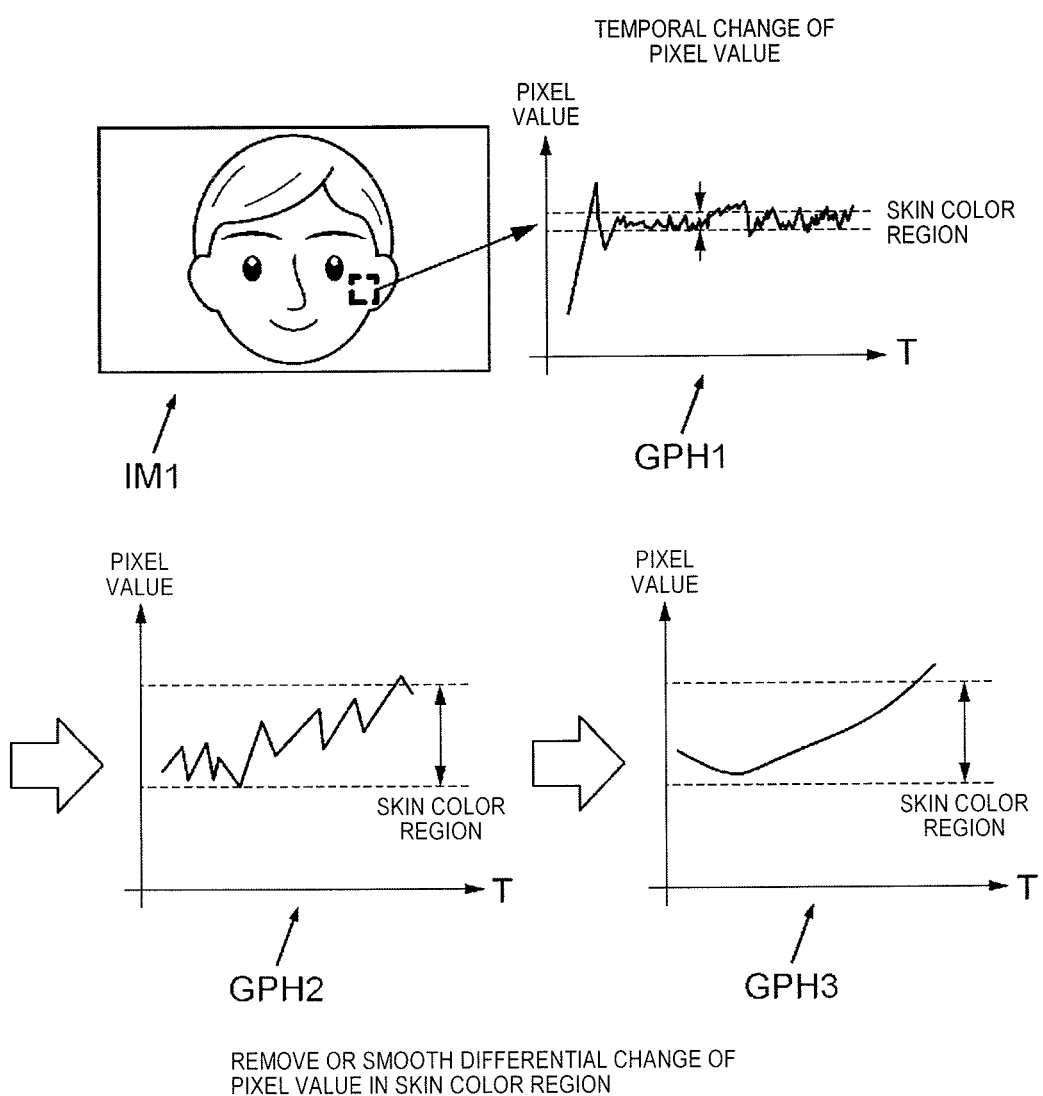

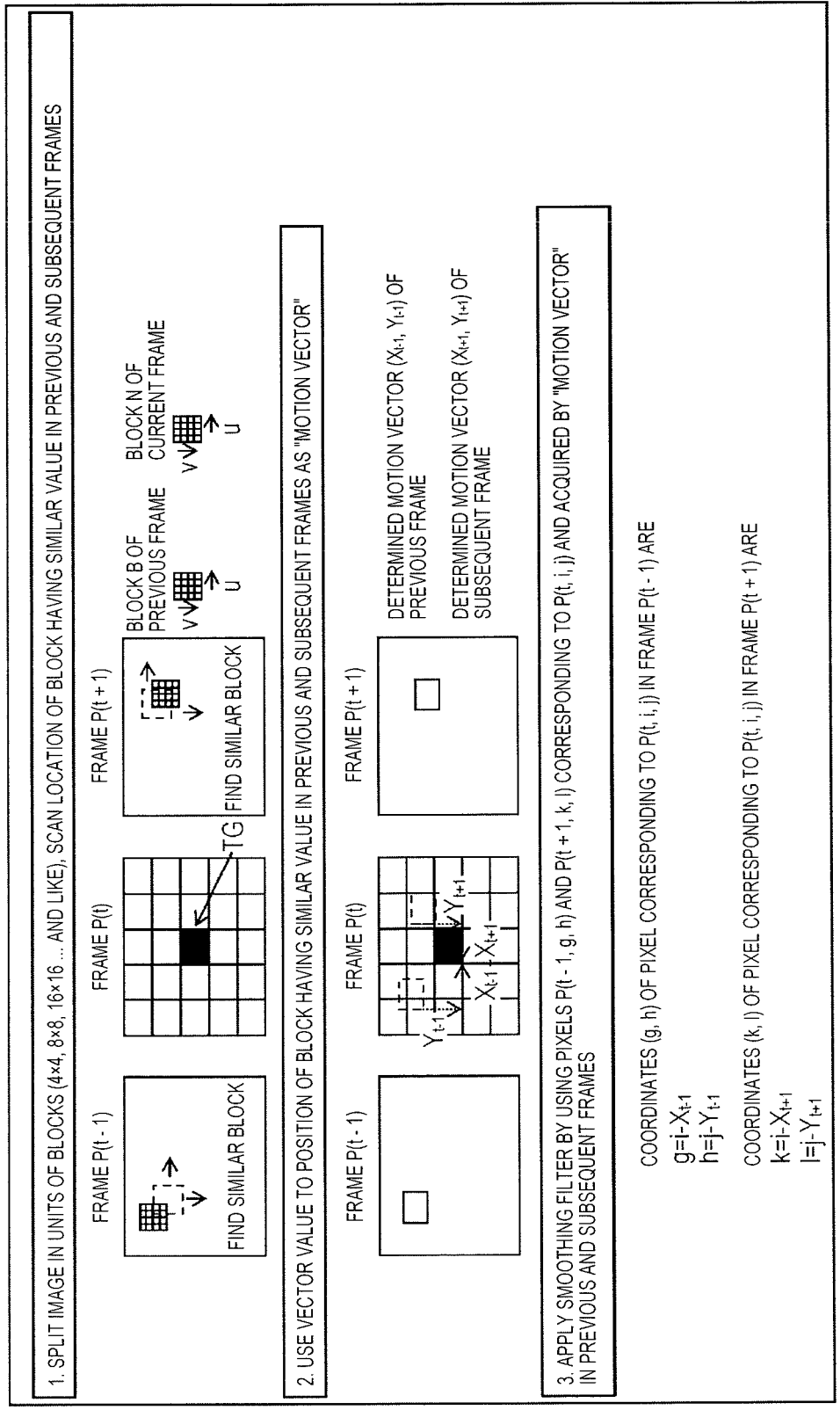

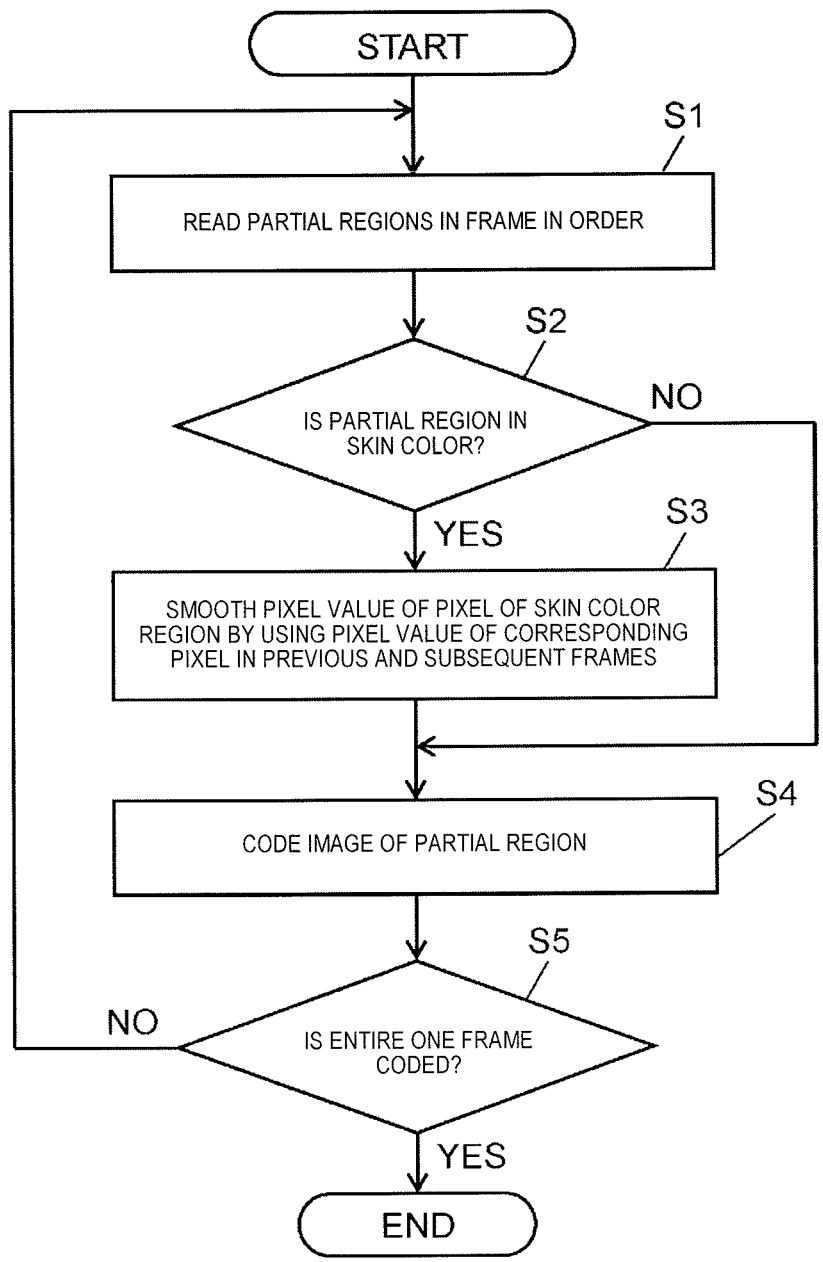

IMAGE CAPTURING APPARATUS, IMAGE PROCESSING APPARATUS AND IMAGE PROCESSING METHOD FOR SECURE PROCESSING OF BIOLOGICAL INFORMATION

TECHNICAL FIELD

The present disclosure relates to an image capturing apparatus, an image processing apparatus, and an image processing method performing image processing of an image.

BACKGROUND ART

A vital sensing technology that estimates biological information of a human being is expected to be applied to, for example, not only a field of in-home healthcare or health management but also multiple types of fields such as drowsiness detection during driving, acquisition of a mental state of a user during a game, and detection of a suspicious person in a monitoring system. Currently, a main type of device that senses the biological information is used in contact with a human body and is required to be mounted by a user. Thus, the range of applications thereof is limited.

Thus, as one of measures for contactless sensing, suggested is a technology that estimates a pulse as one example of the biological information from an image acquired by capturing of a camera. Using this technology enables sensing of the biological information without causing the user to be aware thereof, and the range of applications of the technology is expected to be increased. For example, performing image processing of an image acquired by capturing along with performing capturing with a monitoring camera enables sensing of a suspicious person who has a significantly changing pulse by stress. Being able to sense a plurality of human beings represented on one camera at the same time by image processing is also a great advantage. Individual devices are not required to be prepared per user compared with a contact type, and inconvenience of attaching the device to the body can be reduced.

For example, a pulse measurement device illustrated in PTL 1 is known as a preceding technology related to the pulse estimation technology using a camera. The pulse measurement device calculates the amount of features of a captured input image, detects peak intervals of a pulse wave from the calculated amount of features, and calculates pulse rates from the detected peak intervals of the pulse wave. The pulse measurement device controls a frame rate that indicates the number of frames captured per unit time, in such a manner that the maximum estimation error between true pulse rates and pulse rates, of the calculated pulse rates, having a valid peak interval based on an adoption rate indicating the proportion of a valid peak interval is less than or equal to a defined value.

However, if the image quality of the image captured by the camera is increased (by, for example, 4K or super hi-vision (8K)), image processing of, for example, a broadcasting video content may cause a viewer to recognize the pulse rate of a human being appearing in the video content (for example, a participant), and it is difficult to properly protect the privacy of the participant.

For example, the broadcasting video content can be received and viewed with a personal computer (PC). Thus, if an application that estimates a pulse rate by above image processing is installed and used in the PC, the pulse rate of the participant may be simply recognized from an image processing result, and this is not preferable from the viewpoint of privacy.

An object of the present disclosure is to effectively reduce distribution of biological information not intended by a producer or a distributor of a video content and to properly protect the privacy of a human being appearing in the video content.

CITATION LIST

Patent Literature

PTL 1: Japanese Patent Unexamined Publication No. 2010-51592

SUMMARY OF THE INVENTION

An image processing apparatus of the present disclosure includes an image input that receives input of image data of a captured human being, a region detector that detects a specific color region of the image data, a filter that smooths a pixel value in the specific color region detected by the region detector by using a frame of the image data input into the image input and each of previous and subsequent frames of the image data of the inputting into the image input, a coder that codes an output image of the filter, and an output that outputs the output image of the filter coded by the coder.

An image capturing apparatus of the present disclosure includes an image capturer that captures a human being as a subject, a region detector that detects a specific color region of image data including the human being captured by the image capturer, a filter that smooths a pixel value in the specific color region detected by the region detector by using a frame of the image data captured in the image capturer and each of previous and subsequent frames of the image data of the capturing in the image capturer, a coder that codes an output image of the filter, and an output that outputs the output image of the filter coded by the coder.

Furthermore, an image processing method of the present disclosure is an image processing method in an image processing apparatus and has a step of inputting image data of a captured human being, a step of detecting a specific color region of the image data, a step of smoothing a pixel value in the detected specific color region by using a frame of the input image data and each of previous and subsequent frames of the image data of the inputting, a step of coding an output image in which the pixel value in the specific color region is smoothed, and a step of outputting the coded output image.

According to the present disclosure, distribution of biological information that is not intended by a producer or a distributor of a video content can be effectively reduced, and the privacy of a human being appearing in the video content can be properly protected.

BRIEF DESCRIPTION OF DRAWINGS

FIG. 5B is a descriptive diagram related to detection of a skin color region of a human being.

FIG. 6 is a descriptive diagram illustrating a summary of operation of a photoelectric pulse wave change removal filter.

FIG. 8 is a descriptive diagram illustrating an operation example of the photoelectric pulse wave change removal filter in the case of a human being of a subject moving.

FIG. 9 is a flowchart describing one example of an operation procedure of an image processing apparatus of the present exemplary embodiment.

DESCRIPTION OF EMBODIMENT

Hereinafter, an exemplary embodiment in which an image capturing apparatus, an image processing apparatus, and an image processing method according to the present disclosure are specifically disclosed (hereinafter, referred to as a "present exemplary embodiment") will be described with reference to the drawings. The image capturing apparatus of the present exemplary embodiment is, for example, a digital still camera (DSC); a digital camcorder; a smartphone, a mobile telephone, or a tablet terminal having camera function; or a monitoring camera. The image processing apparatus of the present exemplary embodiment is, for example, an electronic apparatus in which an encoder application is installed (for example, a desktop or laptop PC), an encoder apparatus as a dedicated apparatus, or a recorder.

Hereinafter, while the present exemplary embodiment will illustrate the image processing apparatus and describe operation of the image processing apparatus, description of the image processing apparatus can be applied in the same manner to description of the image capturing apparatus except for description that is based on difference between configurations of the image processing apparatus and the image capturing apparatus. The image processing apparatus of the present exemplary embodiment receives input of image data of a captured human being from an external unit (for example, an external device that is connected to the image processing apparatus) and detects a specific color region of the input image data. A frame of the input image data and each of the previous and subsequent frames of the image data at the point in time of the inputting are used to smooth a pixel value in the specific color (for example, skin color) region in the frame of the image data. While, for example, averaging processing that uses the pixel value of the specific color region corresponding to the previous and subsequent frames is used as one example of the smoothing, details will be described later. The image processing apparatus codes an output image after smoothing of the pixel value and outputs the coded output image to an external unit (for example, an external device connected to a network or a display).

Figure 1A:
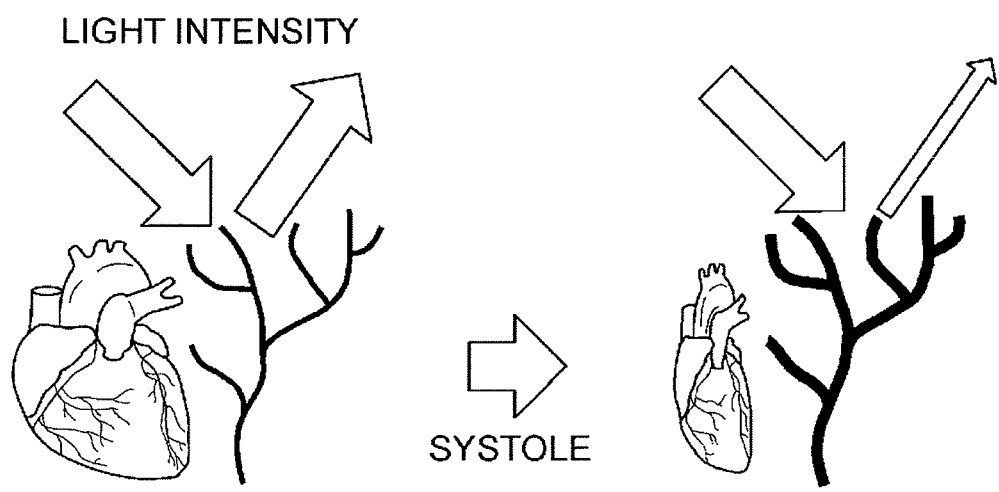
FIG. 1A is a diagram schematically illustrating one example of a relationship between systole of a heart of a human being and the amount of light absorbed in a blood vessel.
Figure 1B:
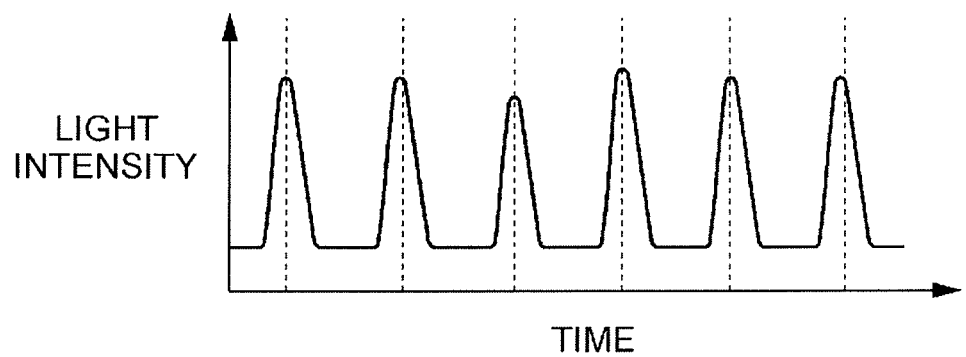
FIG. 1B is a diagram illustrating one example of time-series change in light intensity.

First, a pulse rate estimation principle in the image processing apparatus or the image capturing apparatus of the present exemplary embodiment will be described with reference to FIG. 1A and FIG. 1B. FIG. 1A is a diagram schematically illustrating one example of a relationship between systole of a heart of a human being and the amount of light absorbed in a blood vessel. FIG. 1B is a diagram illustrating one example of time-series change in light intensity.

FIG. 1A illustrates change in the volume of the blood vessel in synchronization with systole of the heart of the human being. If the volume of the blood vessel is increased in response to systole of the heart, the amount of absorbed light (for example, light in a specific wavelength region illustrated in FIG. 2) is increased. Thus, light intensity is decreased (refer to FIG. 1B). A pulse wave represents a motion of a wave when change in pressure in the blood vessel generated at the time of blood being pushed to a great artery by systole of the heart is transmitted in a peripheral direction.

In FIG. 1B, the horizontal axis denotes time, and the vertical axis denotes the intensity of a signal (photoelectric pulse wave) that is acquired by change in the amount of absorbed light. That is, in FIG. 1B, when a peak appears, the amount of absorbed light is small, and thus, the volume of the blood vessel is in a non-increased state. When a minimum value appears, the amount of absorbed light is large, and thus, the volume of the blood vessel is in an increased state. While slight delays are found with incomplete synchronization due to the distance between the heart and a peripheral part, systole of the heart is basically changed in synchronization with change in the intensity of the photoelectric pulse wave.

Figure 2:
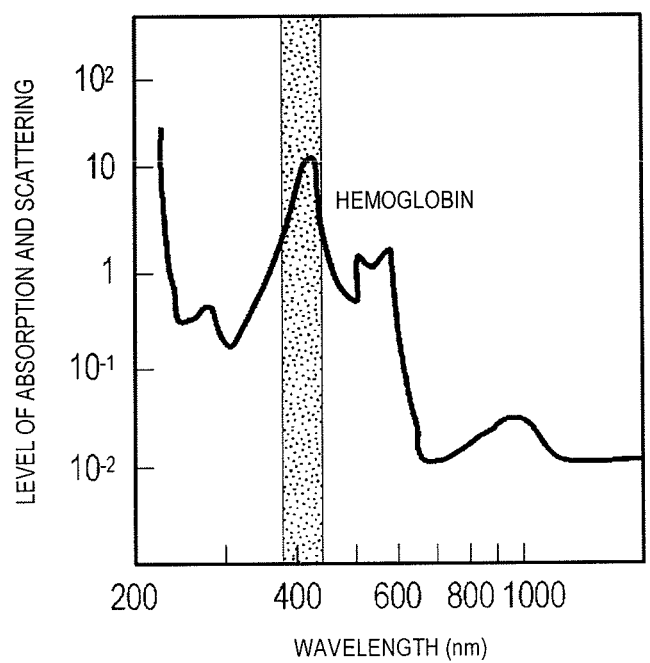
FIG. 2 is a diagram illustrating one example of absorbance of light per wavelength in hemoglobin.

FIG. 2 is a diagram illustrating one example of absorbance of light per wavelength in hemoglobin. In FIG. 2, for example, hemoglobin (blood) is illustrated as being likely to absorb a wavelength of 400 nm (that is, green). In the present exemplary embodiment below, the image processing apparatus will be described as smoothing the pixel value of the specific color (for example, skin color) region in one frame constituting the image data acquired by capturing, in order to properly protect the privacy of the captured human being (for example, a participant in a television program). The specific color is not limited to skin color. For example, the image processing apparatus may smooth the pixel value of a red (a wavelength exceeding 1,000 nm illustrated in FIG. 2) region.

Figure 3:
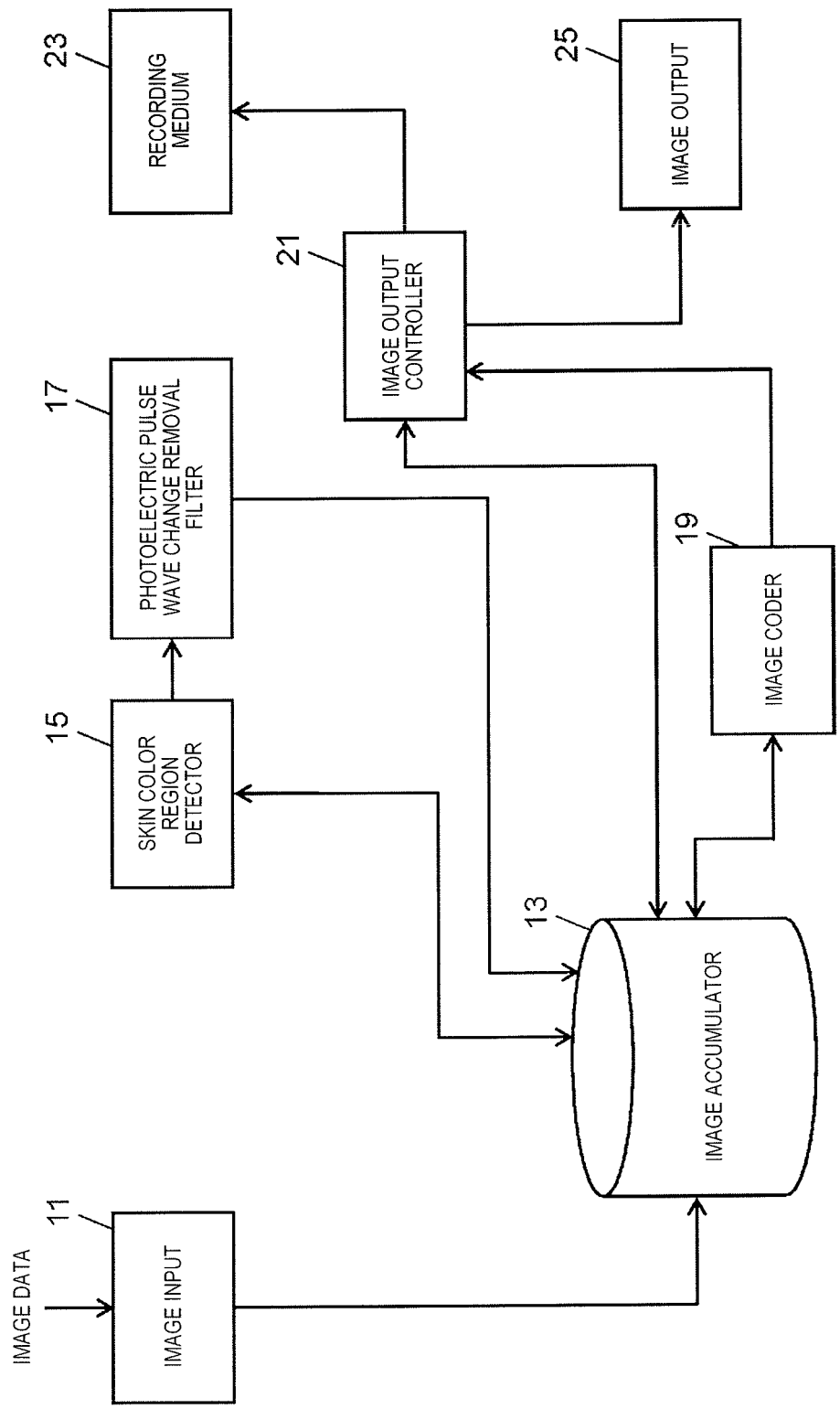
FIG. 3 is a block diagram illustrating one example of an internal configuration of an image processing apparatus of a present exemplary embodiment.
Figure 4:
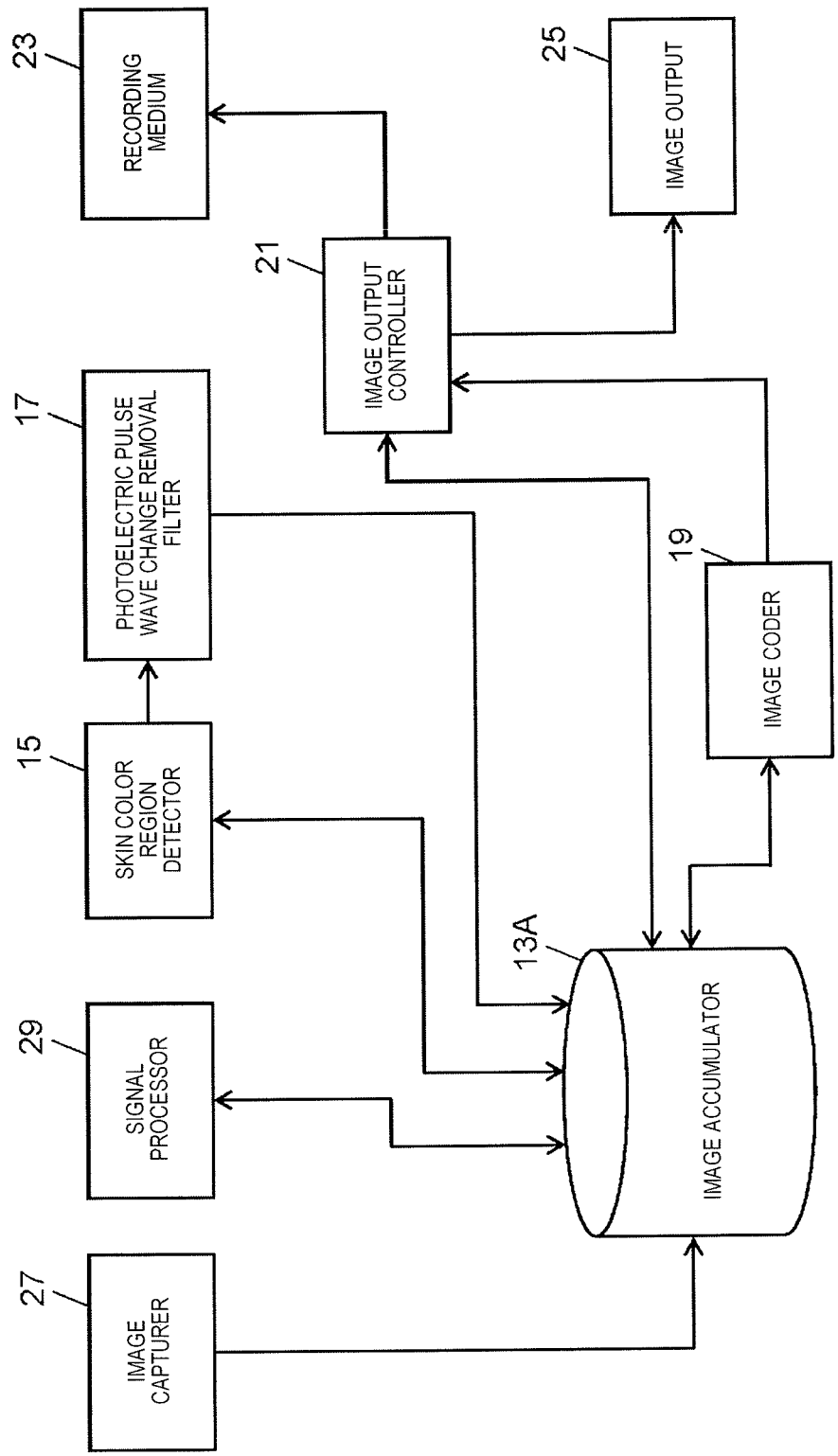
FIG. 4 is a block diagram illustrating one example of an internal configuration of an image capturing apparatus of the present exemplary embodiment.

First, configurations of image processing apparatus 1 and image capturing apparatus 1A of the present exemplary embodiment will be described with reference to FIG. 3 and FIG. 4. FIG. 3 is a block diagram illustrating one example of an internal configuration of image processing apparatus 1 of the present exemplary embodiment. FIG. 4 is a block diagram illustrating one example of an internal configuration of image capturing apparatus 1A of the present exemplary embodiment. In FIG. 4, the same constituents as each unit of image processing apparatus 1 illustrated in FIG. 3 are designated by the same reference signs, and descriptions thereof will be simplified or will not be provided.

Image processing apparatus 1 illustrated in FIG. 3 is configured to include image input 11, image accumulator 13, skin color region detector 15, photoelectric pulse wave change removal filter 17, image coder 19, image output controller 21, recording medium 23, and image output 25.

Image capturing apparatus 1A illustrated in FIG. 4 is configured to include image capturer 27, image accumulator 13A, signal processor 29, skin color region detector 15, photoelectric pulse wave change removal filter 17, image coder 19, image output controller 21, recording medium 23, and image output 25.

Image input 11 successively receives (acquires), from an external device, input of frames of image data of a human being (for example, a participant in a television program) captured by the external device (for example, a camera that performs capturing at a predetermined frame rate) not illustrated, and retains the frames in image accumulator 13.

Image accumulator 13 as one example of a storage is configured by using a semiconductor memory such as a dynamic random access memory (DRAM) or a hard disk and retains the image data input by image input 11 and image data of an output image of photoelectric pulse wave change removal filter 17.

Figure 5A:
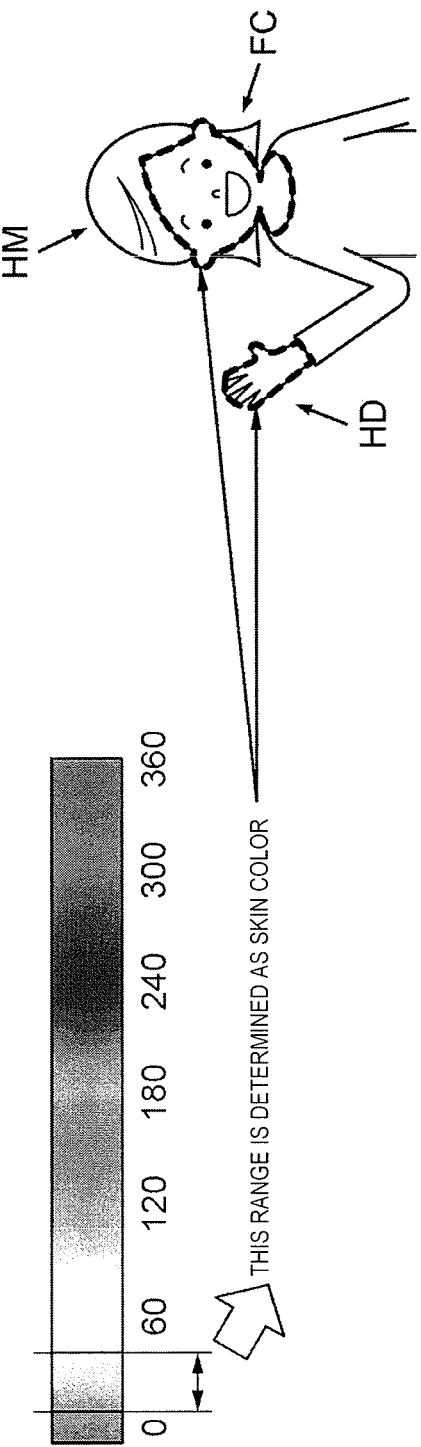
FIG. 5A is a descriptive diagram related to detection of a skin color region of a human being.

Skin color region detector 15 as one example of a region detector reads the image data retained in image accumulator 13 by image input 11 and detects a specific color (for example, skin color) region (for example, face region FC and hand region HD of human being HM illustrated in FIG. 5A and FIG. 5B) in the frame of the image data. Skin color region detector 15 outputs, to photoelectric pulse wave change removal filter 17, information (for example, coordinates) that is related to the specific color region detected in the frame of the image data. A detection method for the specific color (for example, skin color) region in skin color region detector 15 will be described later with reference to FIG. 5A and FIG. 5B.

Photoelectric pulse wave change removal filter 17 as one example of a filter reads, per partial region, the image data retained in image accumulator 13 by image input 11 and uses the pixel value of the partial region of the frame of the image data input by image input 11 and the pixel values of the corresponding partial regions of each of the previous and subsequent frames of the image data of the inputting into image input 11 to smooth the pixel value of the image data of the specific color region detected by skin color region detector 15 (refer to FIG. 6). The pixel value is represented by luminance (Y) and chrominance (U, V). Photoelectric pulse wave change removal filter 17 retains, in image accumulator 13, the image data after smoothing of the pixel value of the image data of the specific color region. A smoothing method in photoelectric pulse wave change removal filter 17 will be described later with reference to FIG. 6 to FIG. 8.

Image coder 19 as one example of a coder uses the image data of the output image of photoelectric pulse wave change removal filter 17 retained in image accumulator 13 (that is, the image data having the pixel value of the specific color region smoothed by photoelectric pulse wave change removal filter 17) to generate coded data for conversion into a predetermined data format that enables retaining and sending of the image data. Image coder 19 outputs the coded data of the image data to image output controller 21.

The image data coded by image coder 19 is retained in recording medium 23 or output to image output 25 by image output controller 21.

Recording medium 23 as one example of a recording unit is configured by using a semiconductor memory such as a DRAM or a hard disk, and the coded data of the image data generated by image coder 19 is recorded in recording medium 23. Recording medium 23 is not limited to the semiconductor memory or the hard disk incorporated into image processing apparatus 1 or image capturing apparatus 1A and may be, for example, an externally connected medium (for example, a semiconductor such as a DRAM) that can be connected through a Universal Serial Bus (USB) terminal.

Image output 25 as one example of an output, in accordance with an instruction of image output controller 21, uses the coded data of the image data generated by image coder 19 to perform, for example, packet generation processing for sending to an external device (not illustrated) of a sending destination and sends the packet of the coded data of the image data to the external device. Accordingly, image output 25 can send the image data having the smoothed pixel value of the specific color region (in other words, the image data for which analysis of the pulse rate of the human being appearing in the image data is difficult) to the external device.

The network is a wireless network or a wired network. The wireless network is, for example, near field communication (NFC), Bluetooth (registered trademark), IrDA, a wireless local area network (LAN), 3G, Long Term Evolution (LTE), or WiGig. The wired network is, for example, an intranet or the Internet.

Image output 25, in accordance with an instruction of image output controller 21, displays the image data of the output image of photoelectric pulse wave change removal filter 17 retained in image accumulator 13 (that is, the image data having the pixel value of the specific color region smoothed by photoelectric pulse wave change removal filter 17) on, for example, a display (not illustrated).

In image capturing apparatus 1A illustrated in FIG. 4, image capturer 27 is configured to include at least a lens and an image sensor for capturing a human being as a subject (for example, a participant in a television program). The lens (not illustrated) condenses ambient light incident from the outside of image capturing apparatus 1A and forms an image of the light on a predetermined image capturing surface of the image sensor (not illustrated).

The image sensor is configured by using a solid state image capturing element such as a charged-coupled device (CCD) or a complementary metal oxide semiconductor (CMOS) and converts the optical image formed on the image capturing surface into an electrical signal. The output of the image sensor is input and retained in image accumulator 13A.

Image accumulator 13A as one example of a storage is configured by using a semiconductor memory such as a DRAM or a hard disk and retains the output of the image sensor of image capturer 27 and the image data of the output image of photoelectric pulse wave change removal filter 17.

Signal processor 29 uses the output of the image sensor retained in image accumulator 13A to generate a frame of image data in red, green, and blue (RGB) format recognizable by the human being or of image data defined by luminance (Y) and chrominance (U,V) (YUV) and retains the generated frame in image accumulator 13A.

Next, a method for skin color region detector 15 detecting the specific color (for example, skin color) region in the frame of the image data will be described with reference to FIG. 5A and FIG. 5B. FIG. 5A and FIG. 5B are descriptive diagrams related to detection of the skin color region of the human being. In FIG. 5A and FIG. 5B, for example, two types of methods will be described as the method for skin color region detector 15 detecting the specific color (for example, skin color) region in the frame of the image data.

In a first example, skin color region detector 15 determines, as skin color, color of which the pixel value (for example, chrominance) in the frame of the image data is included in a previously specified range (for example, a predetermined range between 0 and 60) in HSV color space. Therefore, skin color region detector 15 detects, as the skin color region, face region FC and hand region HD in the image data representing human being HM illustrated in FIG. 5A.

In a second example, skin color region detector 15 performs, based on a luminance signal, image processing (for example, face detection processing) of the frame of the image data representing human being HM illustrated in FIG. 5B to detect the face of human being HM and determines, as skin color, the color of a region that has the same chrominance as detected face region FC or chrominance within a predetermined range from the chrominance of face region FC. Therefore, skin color region detector 15 detects, as the skin color region, hand region HD having the same or similar (equivalent) chrominance as face region FC in the image data representing human being HM illustrated in FIG. 5B.

Figure 7:
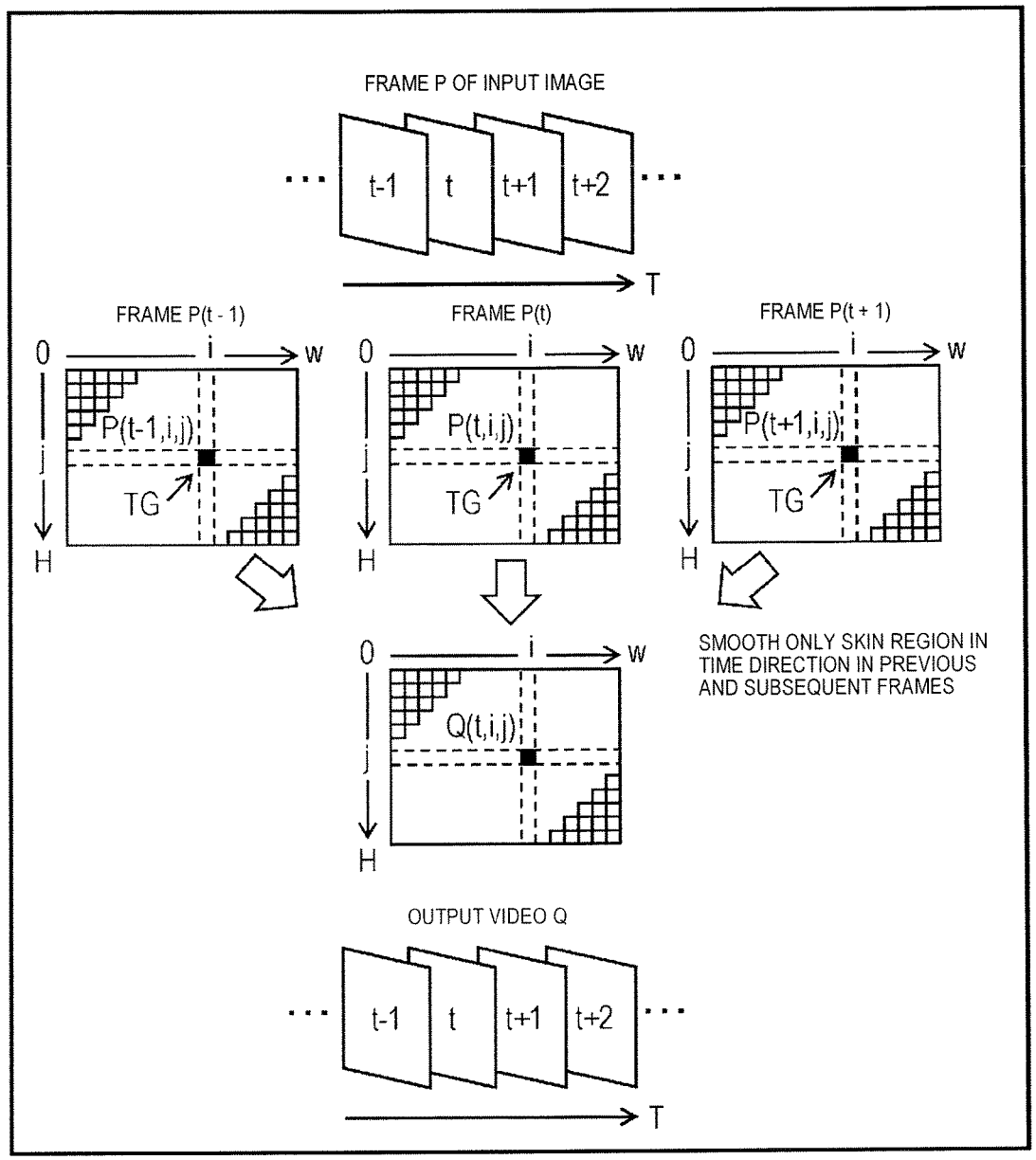
FIG. 7 is a descriptive diagram illustrating an operation example of the photoelectric pulse wave change removal filter in the case of a human being of a subject being still.

Next, processing of photoelectric pulse wave change removal filter 17 smoothing the pixel value of the specific color (for example, skin color) region will be described with reference to FIG. 6 to FIG. 8. FIG. 6 is a descriptive diagram illustrating a summary of operation of photoelectric pulse wave change removal filter 17. FIG. 7 is a descriptive diagram illustrating an operation example of photoelectric pulse wave change removal filter 17 in the case of a human being of a subject being still. FIG. 8 is a descriptive diagram illustrating an operation example of photoelectric pulse wave change removal filter 17 in the case of a human being of a subject moving.

As illustrated in FIG. 6, photoelectric pulse wave change removal filter 17 executes removing and smoothing a differential change of the pixel value of the skin color region (refer to graph GPH1 illustrated in FIG. 6) for a frame of image data IM1 from which the skin color region of the human being is detected by skin color region detector 15. The pixel value may be the average value of pixel values in one block that can be configured of (one pixel×one pixel) or (32 pixels in the horizontal direction of the frame×32 pixels in the vertical direction of the frame). The number of pixels constituting one block is not limited to (32 in the horizontal direction of the frame×32 in the vertical direction of the frame).

Accordingly, the differential change of the pixel value of the skin color region with respect to time T illustrated in graph GPH1 is gradually smoothed and lessened (refer to graphs GPH2 and GPH3). In other words, it is difficult to infer the original data of the pixel value of the skin color region, and consequently, it is difficult to estimate the pulse rate. Thus, the privacy of the human being represented in the frame of image data IM1 can be properly protected.

The operation example of photoelectric pulse wave change removal filter 17 will be more specifically described by illustrating a still state of the human being of the subject with reference to FIG. 7. In FIG. 7, frame P of an image input by image input 11 (input image) is successively input per time T. Photoelectric pulse wave change removal filter 17 smooths pixel value P(t,i,j) of specific color (for example, skin color) region TG by using frame P(t) input at time T=t and frames P(t−1) and P(t+1) input at previous time and subsequent time T=(t−1) and T=(t+1) of the inputting.

Specifically, photoelectric pulse wave change removal filter 17, as time-direction smoothing of pixel value P(t,i,j) of specific color (for example, skin color) region TG, calculates the average value of pixel value P(t,i,j) of specific color (for example, skin color) region TG in frame P(t) and pixel values P(t−1,i,j) and P(t+1,i,j) of specific color (for example, skin color) region TG in corresponding frames P(t−1) and P(t+1) (refer to Equation (1)). Photoelectric pulse wave change removal filter 17 does not execute smoothing by Equation (1) for the pixel value of other than specific color (for example, skin color) region TG.

In Equation (1), Q(t,i,j) denotes smoothed output of pixel value P(t,i,j) of specific color (for example, skin color) region TG in frame P(t) in photoelectric pulse wave change removal filter 17. In Equation (1), P(t,i,j) denotes the pixel value at coordinates (i,j) in frame P(t) that is input at time T=t.

$$Q(t, i, j) = \frac{P(t-1, i, j) + P(t, i, j) + P(t+1, i, j)}{3} \tag{1}$$

Photoelectric pulse wave change removal filter 17, in the case of the difference between the pixel value of the specific color region in frame P(t) at time T=t and the pixel values of the corresponding specific color regions in frames P(t−1) and P(t+1) at time T=(t−1) and (t+1) being greater than a predetermined value (for example, four), does not execute smoothing of the pixel value in the specific color region in frame P(t) at time T=t and outputs the pixel value. Accordingly, since a motion clearly appears in frame P(t) at the point in time of the inputting by image input 11, photoelectric pulse wave change removal filter 17 can reduce influence on the image quality of the frame (for example, image quality degradation) by not performing smoothing using frame P(t) at the point in time of the inputting and each of previous and subsequent frames P(t−1) and P(t+1) of the inputting.

Next, the operation example of photoelectric pulse wave change removal filter 17 will be more specifically described by illustrating a moving state of the human being of the subject with reference to FIG. 8. In FIG. 8, frame P of the image input by image input 11 (input image) is successively input per time T as in FIG. 7. Photoelectric pulse wave change removal filter 17 smooths pixel value P(t,i,j) of specific color (for example, skin color) region TG by using frame P(t) input at time T=t, frames P(t−1) and P(t+1) input at previous time and subsequent time T=(t−1) and T=(t+1) of the inputting, and motion vectors of the specific color (for example, skin color) region that are generated between frame P(t) and the adjacent previous and subsequent frames.

Specifically, photoelectric pulse wave change removal filter 17 splits the frame of the image data in units of blocks (for example, 4 pixels×4 pixels, 8 pixels×8 pixels, 16 pixels×16 pixels, . . . ) and finds the locations of blocks having the same or similar pixel value in the adjacent previous and subsequent frames by scanning in units of blocks. For example, photoelectric pulse wave change removal filter 17 calculates the sum of the absolute values of the differences of the pixel value illustrated in Equation (2) for block B of the previous frame (frame at time T=(t−1)) and block N of the current frame (frame at time T=t). Photoelectric pulse wave change removal filter 17 determines, as blocks having the same or similar pixel value as the specific color (for example, skin color) region of the current frame in the adjacent previous and subsequent frames, a block from which the minimum value of the sum of the absolute values of the differences of the pixel value in corresponding positions in the blocks is acquired.

$$\sum_{u=0,v=0} |Nuv - Buv| \tag{2}$$

Next, photoelectric pulse wave change removal filter 17 calculates, as the motion vectors, vector values to the positions of blocks having the same or similar pixel value in the adjacent previous and subsequent frames. In FIG. 8, the motion vector for the previous frame (that is, the frame at time T=(t−1)) calculated by photoelectric pulse wave change removal filter 17 is denoted by (X(t−1),Y(t−1)), and the motion vector for the subsequent frame (that is, the frame at time T=(t+1)) calculated by photoelectric pulse wave change removal filter 17 is denoted by (X(t+1),Y(t+1)).

Photoelectric pulse wave change removal filter 17 uses the calculated motion vectors to calculate the average value of pixel value P(t,i,j) of the specific color (for example, skin color) region in frame P(t) at time T=t and corresponding pixel value P(t−1,g,h) and pixel value P(t+1,k,l) in the previous and subsequent frames adjacent to time T=t (that is, each frame at time T=(t−1) and T=(t+1)) (refer to Equation (3)). Photoelectric pulse wave change removal filter 17 does not execute smoothing by Equation (3) for the pixel value of other than specific color (for example, skin color) region TG.

$$Q(t, i, j) = \frac{P(t-1, g, h) + P(t, i, j) + P(t+1, k, l)}{3} \quad (3)$$

In Equation (3), coordinates (g,h), in frame P(t−1) at time T=(t−1), of the pixel value corresponding to pixel value P(t,i,j) of the specific color (for example, skin color) region in frame P(t) at time T=t are represented by Equation (4). Similarly, in Equation (3), coordinates (k,l), in frame P(t+1) at time T=(t+1), of the pixel value corresponding to pixel value P(t,i,j) of the specific color (for example, skin color) region in frame P(t) at time T=t are represented by Equation (5).

$$(g,h) = (i - X_{(t-1)}, j - Y_{(t-1)}) \quad (4)$$

$$(k,l) = (i - X_{(t+1)}, j - Y_{(t+1)}) \quad (5)$$

Next, an operation procedure for removing photoelectric pulse wave change in image processing apparatus 1 of the present exemplary embodiment will be described with reference to FIG. 9. FIG. 9 is a flowchart describing one example of an operation procedure of image processing apparatus 1 of the present exemplary embodiment.

In FIG. 9, image input 11 successively receives (acquires), from an external device, input of frames of image data of a human being (for example, a participant in a television program) captured by the external device (for example, a camera that performs capturing at a predetermined frame rate) not illustrated, and retains the frames in image accumulator 13. Skin color region detector 15 reads the image data retained in image accumulator 13 by image input 11 and detects a specific color (for example, skin color) region (for example, face region FC and hand region HD of human being HM illustrated in FIG. 5A and FIG. 5B) in the frame of the image data. Skin color region detector 15 outputs, to photoelectric pulse wave change removal filter 17, information (for example, coordinates) that is related to the specific color region detected in the frame of the image data.

Photoelectric pulse wave change removal filter 17 reads, per partial region, the image data retained in image accumulator 13 by image input 11 (S1) and determines whether or not the read partial region is in skin color based on the output of skin color region detector 15 (that is, information (for example, coordinates) related to the specific color region detected in the frame of the image data) (S2). As described above, the pixel value may be the average value of pixel values in one block that can be configured of (one pixel×one pixel) or (32 pixels in the horizontal direction of the frame×32 pixels in the vertical direction of the frame).

Photoelectric pulse wave change removal filter 17, in the case of the data of the pixel value of the partial region read in Step S1 being equal to previously specified color (for example, skin color) (YES in S2), uses the frame of the partial region read in Step S1 and each of the previous and subsequent frames of the image data of the inputting into image input 11 to smooth the pixel value (more specifically, luminance (Y) and chrominance (U,V)) of the image data of the specific color region detected by skin color region detector 15 (S3).

In the smoothing processing in Step S3, for example, the smoothing processing is performed by the method illustrated in FIG. 7 in the case of the human being represented in the image data being still, and the smoothing processing is performed by the method illustrated in FIG. 8 in the case of the human being represented in the image data moving. Photoelectric pulse wave change removal filter 17 retains, in image accumulator 13, the image data of the partial region after smoothing of the pixel value of the image data of the specific color region.

In the case of the data of the pixel value of the partial region read in Step S1 not being equal to the previously specified color (for example, skin color) (NO in S2), processing of image processing apparatus 1 proceeds to Step S4.

Image coder 19 codes the image data of the output image of photoelectric pulse wave change removal filter 17 retained in image accumulator 13 (that is, the image data of the partial region in which the pixel value of the partial region read in Step S1 is smoothed by photoelectric pulse wave change removal filter 17) (S4).

In the case of the entire one frame being coded (YES in S5), the operation of image processing apparatus 1 illustrated in FIG. 9 is finished. In the case of the entire one frame not being coded (NO in S5), each process of Step S1 to Step S4 is repeated until the entire one frame is coded.

According to the description heretofore, image processing apparatus 1 of the present exemplary embodiment receives input of image data of a captured human being in image input 11, extracts a specific color region of the input image data in skin color region detector 15, and uses a frame of the input image data and each of the previous and subsequent frames of the image data at the point in time of the inputting to smooth a pixel value in the specific color (for example, skin color) region in photoelectric pulse wave change removal filter 17. Image processing apparatus 1 codes the output image of photoelectric pulse wave change removal filter 17 after smoothing of the pixel value and outputs the coded output image to an external unit (for example, an external device connected to a network or a display).

Accordingly, image processing apparatus 1, since smoothing the pixel value in the specific color (for example, skin color) region in the frame of the image data, can effectively reduce distribution of biological information (for example, a pulse rate) not intended by a producer or a distributor of a video content configured of the image data and thus can properly protect the privacy of a human being appearing in the video content. As a more specific example, image processing apparatus 1 can prevent a viewer from recognizing rise of the pulse rate of an announcer who makes a mistake in saying a speech content in the case of the announcer participating in a television program, rise of the pulse rate of a chess player in a Japanese chess game, and the like and enables a producer or a distributor of a video content to produce a video content that can properly protect the privacy of a participant.

In the case of the difference between the pixel value of the specific color region in the frame of the input image data and the pixel values of the corresponding specific color regions in each of the previous and subsequent frames of the image data at the point in time of the inputting being greater than a predetermined value (for example, four), image processing apparatus 1 of the present exemplary embodiment does not execute smoothing the pixel value in the specific color region in the frame of the input image data and outputs the pixel value.

Accordingly, since a motion clearly appears in the frame at the point in time of the inputting by image input 11, image processing apparatus 1 can reduce influence on the image quality of the frame (for example, image quality degradation) by not performing smoothing using the frame at the point in time of the inputting and each of the previous and subsequent frames of the inputting.

In image processing apparatus 1, the average value of a block of a plurality of pixels (for example, 32 pixels) in the horizontal direction and a plurality of pixels (for example, 32) in the vertical direction of the frame of the image data input into image input 11 is used as the pixel value in the specific color region.

Accordingly, image processing apparatus 1, since the average value of the pixel values in units of blocks having a plurality of pixels is used as the pixel value in the specific color region, can improve reliability of the pixel value in the specific color region compared with the case of using the pixel value of a single pixel.

While various exemplary embodiments are described heretofore with reference to the drawings, the present disclosure is obviously not limited to such an example. Those skilled in the art may apparently perceive various modification examples or correction examples within the scope disclosed in the claims, and those examples are obviously understood to fall within the technical scope of the present disclosure.

INDUSTRIAL APPLICABILITY

The present disclosure is useful as an image capturing apparatus, an image processing apparatus, and an image processing method that effectively reduce distribution of biological information not intended by a producer or a distributor of a video content and properly protect the privacy of a human being appearing in the video content.

REFERENCE MARKS IN THE DRAWINGS 1 image processing apparatus
1A image capturing apparatus
11 image input
13, 13A image accumulator
15 skin color region detector
17 photoelectric pulse wave change removal filter
19 image coder
21 image output controller
23 recording medium
25 image output
27 image capturer
29 signal processor

The invention claimed is:
1. An image processing apparatus comprising:
a processor that
receives input of image data of a captured human being;
detects a specific color region of the image data;
smooths a pixel value in the specific color region by using a frame of the image data and each of previous and subsequent frames of the image data;
codes an output image of the smoothed pixel value in the specific color region; and
outputs the coded output image,
wherein, in a case a difference between the pixel value of the specific color region and pixel values of corresponding specific color regions of the previous and subsequent frames of the image data is greater than a predetermined value, the processor does not execute smoothing of the pixel value in the specific color region.
2. The image processing apparatus of claim 1,
wherein the average value of a plurality of pixels in a horizontal direction and a plurality of pixels in a vertical direction of the frame of the image data is used as the pixel value in the specific color region.
3. An image capturing apparatus comprising:
a camera that captures a human being as a subject; and
a processor that
detects a specific color region of image data including the human being captured by the camera;
smooths a pixel value in the specific color region by using a frame of the image data and each of previous and subsequent frames of the image data;
codes an output image of the smoothed pixel value in the specific color region; and
outputs the coded output image,
wherein, in a case a difference between the pixel value of the specific color region and pixel values of corresponding specific color regions of the previous and subsequent frames of the image data is greater than a predetermined value, the processor does not execute smoothing of the pixel value in the specific color region.
4. An image processing method in an image processing apparatus, the method comprising:
inputting image data of a captured human being;
detecting a specific color region of the image data;
smoothing a pixel value in the detected specific color region by using a frame of the input image data and each of previous and subsequent frames of the image data;
coding an output image in which the pixel value in the specific color region is smoothed; and
outputting the coded output image,
wherein, in a case a difference between the pixel value of the specific color region and pixel values of corresponding specific color regions of the previous and subsequent frames of the image data is greater than a predetermined value, the smoothing of the pixel value in the specific color region is not executed.

* * * * *